(12) United States Patent
Holaday (10) Patent No.: US 8,933,092 B2
(45) Date of Patent: *Jan. 13, 2015

(54) METHODS AND COMPOSITIONS COMPRISING SEQUENTIAL ADMINISTRATION OPIOID RECEPTOR AGONISTS

(75) Inventor: John W. Holaday, Bethesda, MD (US)

(73) Assignee: Qrxpharma Limited, Sydney (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/485,909

(22) Filed: May 31, 2012

(65) Prior Publication Data

US 2012/0309779 A1  Dec. 6, 2012

Related U.S. Application Data

(60) Provisional application No. 61/491,675, filed on May 31, 2011.

(51) Int. Cl.
| | | |
|---|---|---|
| *A61K 31/44* | (2006.01) | |
| *A01N 43/42* | (2006.01) | |
| *A61K 45/06* | (2006.01) | |
| *A61K 31/485* | (2006.01) | |

(52) U.S. Cl.
CPC ............... *A61K 45/06* (2013.01); *A61K 31/485* (2013.01)
USPC ........... 514/282; 514/277; 514/279; 514/280; 514/281

(58) Field of Classification Search
CPC .................................................... A61K 31/485
USPC .......................... 514/277, 279, 280, 281, 282
See application file for complete search history.

(56) References Cited

U.S. PATENT DOCUMENTS

| | | | |
|---|---|---|---|
| 6,277,384 B1 * | 8/2001 | Kaiko et al. .................. | 424/400 |
| 6,375,957 B1 * | 4/2002 | Kaiko et al. .................. | 424/400 |
| 6,475,494 B2 * | 11/2002 | Kaiko et al. .................. | 424/400 |
| 6,696,066 B2 * | 2/2004 | Kaiko et al. .................. | 424/400 |
| 7,172,767 B2 * | 2/2007 | Kaiko et al. .................. | 424/468 |
| 7,419,686 B2 * | 9/2008 | Kaiko et al. .................. | 424/489 |
| 7,749,542 B2 * | 7/2010 | Kaiko et al. .................. | 424/489 |
| 8,105,631 B2 * | 1/2012 | Kaiko et al. .................. | 424/489 |
| 8,182,837 B2 * | 5/2012 | Smith ........................... | 424/464 |
| 8,461,171 B2 * | 6/2013 | Holaday et al. ............... | 514/282 |
| 2002/0058673 A1 * | 5/2002 | Kaiko et al. .................. | 514/282 |

\* cited by examiner

*Primary Examiner* — My-Chau T Tran
(74) *Attorney, Agent, or Firm* — Frommer Lawrence & Haug LLP (57) ABSTRACT

Methods and compositions for the alleviation of pain in a patient. The methods and compositions sequentially administer a therapeutically effective amount of first compound having opioid receptor agonist activity, followed by a therapeutic effective amount of a second or subsequent compound(s) having opioid receptor agonist activity, one or more non-opioid analgesic compounds or one or more hybrid opioid compounds, or mixtures thereof. The methods and compositions effectively alleviate pain with a lower incidence of opioid-induced side effects.

28 Claims, 2 Drawing Sheets

METHODS AND COMPOSITIONS COMPRISING SEQUENTIAL ADMINISTRATION OPIOID RECEPTOR AGONISTS

CROSS-REFERENCE TO RELATED APPLICATIONS

This application claims priority to U.S. provisional application Ser. No. 61/491,675, filed May 31, 2011, the entirety of which is incorporated herein by reference.

FIELD OF THE INVENTION

This invention is directed to a method for the alleviation of pain in patients comprising the sequential administration of a first compound having opioid receptor agonist activity followed by one or more second or subsequent opioid receptor agonists or a mixture of an opioid receptor agonist and a non-opioid analgesic compound. The invention is also directed to pharmaceutical compositions that provide sequential administration of opioid receptor agonist compounds, or the opioid compounds and/or non-opioid analgesic compounds.

BACKGROUND OF THE INVENTION

Opioid compounds remain key agents for the treatment of a wide variety of acute and chronic pain. The World Health Organization has recommended morphine as the analgesic of choice for the treatment of severe cancer pain. Additionally, morphine and related opioids are widely used to alleviate moderate to severe pain after surgery or trauma, or associated with medical illness including, but not limited to, solid or blood borne tumors. Patients with apparently similar pain states have large differences in opioid dosing requirements. Factors that contribute to this variability include type of pain (nociceptive, inflammatory, neuropathic or mixed) and its severity, concurrent medications, gender and other genetic aspects, and whether patients are opioid-naive or tolerant.

Unfortunately, the effects produced by morphine and similar opioid compounds make them amenable to abuse and are associated with many undesirable side effects, all mediated through activation of the mu (MOR) and other opioid receptors. They include physical and psychological dependence leading to addiction and other diverse pathophysiological states. Other undesirable side effects associated with the use of opioids include nausea and vomiting, drowsiness, respiratory depression and gastrointestinal and bladder dysfunction.

In addition to the adverse physiological effects listed above, a major associated risk is that repeated daily administrations of morphine or morphine-like opioids will eventually induce significant tolerance to the therapeutic effects of the drug, as well as initiating some degree of physical dependence. Opioid tolerance is a phenomenon whereby chronic exposure to a drug diminishes its anti nociceptive or analgesic effect, or creates the need for a higher dose to maintain its effect.

One undesirable effect of opioid tolerance is that the higher opioid requirements of highly tolerant patients treated for pain increase the likelihood of unpleasant non-analgesic side effects due to greater circulating concentrations of opioids and potentially toxic opioid metabolites (M. T. Smith, Clin. Exp. Pharmacol. Physiol. 27, 524-528 (2000); F. B. Ross & M. T. Smith, Pain, 73, 151-157 (1997)).

There is a need for improved methods and compositions for the effective alleviation of pain in patients while minimizing or avoiding the undesired side effects associated with opioid receptor agonists.

The opioid receptor is thought to have four receptor subtypes named mu (morphine receptor), sigma (the phencyclidine receptor), kappa (the ketocyclazocine receptor) and delta (the endorphinlenkephalin receptor). The biochemical and cellular effects of morphine, including analgesia, are transduced through the mu opioid receptor (MOR), found in high concentrations within the central nervous system (CNS). The World Health Organization's guidelines for the management of chronic cancer pain recommend that clinicians reserve strong opioids such as oxycodone and morphine for the relief of moderate to severe cancer pain (World Health Organization, 1986) and that two strong opioids should not be co-administered, presumably because it is generally thought that all opioids exert their analgesic effects through the same receptor mechanisms in the CNS.

However, recent studies by Maree Smith and co-workers have shown that the antinociceptive effects of structurally related oxycodone and morphine are differentially antagonized by nor-BNI (a κ-selective opioid antagonist) and naloxonazine (selective μ-opioid receptor antagonist), indicating that they produce antinociception through different opioid receptor mechanisms (see F. B. Ross & M. T. Smith, Pain, 73: 151-157 (1997)). Furthermore, it has been found that co-administration of sub-anti nociceptive doses of oxycodone with morphine to rats results in synergistic levels of antinociception (F. B. Ross et al., Pain, 84, 421-428 (2000)). Importantly, it was found that animals that received the sub-antinociceptive doses of oxycodone and morphine were similar to control animals with respect to CNS side effects. Administration of equipotent-doses of either opioid alone resulted in sedation of the rats. This may suggest that co-administration of sub-analgesic or analgesic doses of oxycodone and morphine to patients may provide synergistic antinociceptive relief with a reduction of CNS-related side effects.

It is known that opioid agonists and antagonists bind in different manners to their respective binding sites and potentially influence the agonist or antagonist response of other molecules, when administered in combination. For example, Holaday et al. reported the cross reactivities of kappa and mu agonists and antagonists in a rat endotoxic shock and rat fluorothyl seizure models and the effects on in vivo changes in striatal cyclic adenosine monophosphate (cAMP) (J. Holaday et al., Research Monograph 71, National Institute on Drug Abuse, 173-187). The authors reported that certain mu antagonists prevent the delta antagonists from blocking or reversing delta agonist effects. For example, it was reported that administration of the mu antagonists naloxazone or β-funaltrexamine (β-FNA) prior to the δ-selective antagonist ICI 154,129 or high doses of naloxone in rats subjected to endotoxemia, resulted in the δ-antagonists no longer effectively reversing endotoxic shock hypotension.

Dosaka-Akita et al. reported that administration of the selective kappa opioid agonist U-50,488H, which by itself had no significant effect on respiration or cardiovascular function, antagonized the acidotic, hypoxemic and hypercapnic effects of subsequently administered mu receptor agonist [D-Ala$^2$,N-Methyl-Phe$^4$, Gly-ol]enkephalin (DAMGO). Administration of U-50,488H prior to administration of DAM GO substantially eliminated the effect of DAMGO on arterial pH, PaO$_2$ and PaCO$_2$. Pretreatment with U-50,488H significantly antagonized morphine-induced acidosis, hypercapnemia and hypoxemia. However, pre-treatment with U-50,488H did not antagonize the morphine effect on increased respiratory rate. This observation highlights the complex nature of opioid agonist and antagonist interaction and the unpredictability of the effect of sequentially administering multiple opioid receptor agonists and/or antagonists.

The present invention provides methods and compositions for the alleviation of pain in a patient comprising the sequential administration of mu and/or kappa opioid receptor agonists to the patient. The methods and compositions provided herein are effective for the alleviation of pain while decreasing certain undesirable side effects of opioid analgesics.

SUMMARY OF THE INVENTION

The invention provides methods and compositions for the alleviation of acute or chronic pain in a patient comprising sequentially administering a first opioid receptor agonist followed by one or more compounds having opioid receptor agonist activity, a mixture of compounds with opioid receptor agonist activity, or a mixture of one or more opioid receptor agonist and one or more non-opioid analgesic compounds. The methods and compositions of the invention surprisingly provide effective analgesia to a patient while reducing or eliminating undesired side effects typically experienced with the administration of opioid analgesic compounds. It may be that biological responses to complex opioid receptor interactions are best manifested by the sequential (as opposed to concomitant) occupation of one opioid receptor site followed by another. Preferred embodiments include administration of a first mu or kappa opioid receptor agonist to a patient followed by a second mu or kappa opioid receptor agonist or a mixture of mu and/or kappa receptor agonists. In a particularly preferred embodiment, the invention provides methods and compositions wherein oxycodone is administered to a patient followed by administration of morphine or a mixture of oxycodone and morphine. Pharmaceutical compositions of the invention sequentially deliver an effective dose of a first opioid receptor agonist immediately after administration or within 30 minutes or an hour of administration, followed by a dose of one or more compounds having opioid receptor agonist activity or a mixture of one or more compounds having opioid receptor activity and one or more non-opioid analgesic compounds.

The invention will be better understood by reference to the following detailed description and examples.

DETAILED DESCRIPTION

The present invention provides methods and compositions for the alleviation of acute or chronic pain in a patient comprising sequentially administering a first opioid receptor agonist followed by a second opioid receptor agonist or a mixture of opioid receptor agonists. Also encompassed by the present invention are methods and compositions for the alleviation of pain in a patient that sequentially deliver an initial opioid receptor agonist, followed by one or more non-opioid analgesic compounds or a mixture of one or more non-opioid analgesic compounds and one or more an opioid receptor agonist. The methods and compositions of the invention surprisingly provide effective analgesia to a patient while reducing or eliminating undesired side effects typically experienced with the administration of opioid analgesic compounds. In one embodiment, the invention provides methods and pharmaceutical compositions that sequentially deliver effective concentrations of two or more opioid receptor agonists and/or non-opioid analgesic compounds to the bloodstream of a patient for the alleviation of acute or chronic pain.

The compositions and methods of the present invention include pharmaceutically acceptable salts of the active agents as well as pharmaceutically acceptable esters or prodrugs of the compounds. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound.

Any of the compounds described herein can be administered as a prodrug to increase the activity, bioavailability, stability or otherwise alter the properties of the compound. A number of prodrug ligands are known. In general, alkylation, acylation or other lipophilic modification of the compound will increase the stability of the compound. Examples of substituent groups that can replace one or more hydrogens on the compound are alkyl, aryl, steroids, carbohydrates, including sugars, 1,2-diacylglycerol and alcohols. Many are described in Jones et al. (R. Jones et al., Antiviral Research, 27, 1-17 (1995)). Any of these can be used in combination with the disclosed compounds to achieve a desired effect.

Definitions

The terms used in herein are intended to have their customary meaning in the art, unless otherwise indicated.

The term "opioid receptor agonist" as used herein refers to a compound that activates an opioid receptor, including mu, kappa, sigma and delta opioid receptors and receptor subtypes.

The term "sequentially" or "sequentially administered" as used herein is intended to mean that a first opioid receptor agonist is administered before one or more subsequently administered active agents or that a first opioid receptor agonist is released into the bloodstream at a faster rate than other active agents so that the first receptor agonist binds the corresponding opioid receptor before the subsequently administered active agents bind their corresponding receptor to any significant extent. In various embodiments, the first opioid receptor agonist is administered 10 minutes, 20 minutes, 30 minutes or 45 minutes before the subsequently administered active agents. In other embodiments, the first opioid receptor agonist is administered 1 hour, 2 hours or 3 hours before the other active agents. In still other embodiments, the first opioid receptor agonist is administered 4 hours, 5 hours or 6 hours before the other active agents.

The term "immediate release formulation" or "immediate release dosage" is intended to have its customary meaning in the art, including a formulation of an active agent that begins to release an effective amount of the active agent into the blood stream immediately after consumption or within 15 minutes, 30 minutes or 1 hour after consumption.

The term "controlled release formulation" or "controlled release dosage" is intended to have its customary meaning in the art, including a formulation of an active agent that releases an effective amount of the active agent into the blood stream later than the corresponding immediate release formulation and continues to release an effective amount of the compound into the blood stream for a longer period, as demonstrated by a longer half life in the blood stream.

Unless otherwise stated, compounds used in the inventive compositions and methods are also meant to include all stereochemical forms of the structure; i.e., the R and S configurations for each asymmetric center. Therefore, single stereochemical isomers, as well as enantiomeric and diastereomeric mixtures of the present compounds, are within the scope of the invention.

Whenever a range is referred to herein, it includes independently and separately every member of the range. As a non-limiting example, 1-10% includes independently, 1%, 2%, 3%, 4%, 5%, 6%, 7%, 8%, 9% and 10%, as well as ranges in between such as 1-2%, 2-3%, etc.

Sequential Administration

The methods and compositions described herein are used to treat different types of pain, including neuropathic pain and nociceptive pain, somatic pain and visceral pain. In various embodiments, methods and compositions described herein are used to treat diabetic neuropathy, trigeminal neuralgia, postherpetic zoster pain, and thalamic pain syndrome (a central pain). Neuropathic pain frequently coexists with nociceptive pain, and the inventive compounds and salts may be used to treat mixed pain states, i.e., a combination of neuropathic and nociceptive pain. For example, trauma that damages tissue and nerves, burns (that burn skin as well as nerve endings), and external nerve compression may cause both neuropathic and nociceptive pain. Examples of external nerve compression include tumor nerve compression and sciatica from herniated discs pressing on nerves. In other embodiments, the inventive compositions are used to treat low back pain, cancer pain, osteoarthritis pain, fibromyalgia pain and postoperative pain. In various other embodiments, the inventive compositions are used to treat pain associated with inflammation, bone pain, and joint disease. The compositions of the invention may be used to treat pain caused by a variety of conditions, including, but not limited to, pain after surgery or trauma, pain associated with a medical illness and the like.

Pre-clinically, an amount effective to act as an opioid agonist is an amount that is found to measurably bind the opioid receptor. The opioid receptor includes the receptor subtypes mu (morphine receptor), sigma (phencyclidine receptor), kappa (the ketocyclazocine receptor) and delta (the endorphinlenkephalin receptor) as well as further classified receptor subtypes. The in vivo antinociceptive activity of the inventive compositions in laboratory animals is evaluated using the widely-accepted Tail Flick Latency Test (F. E. D'Armour et al. J. Pharmacol. Exp. Ther., 72, 74-79 (1941)).

Additional tests of analgesic responsiveness include the paw withdrawal and hotplate tests, i.e., methods well-established as common in the art. Preclinical testing of analgesia and tolerance development is conducted by administration of the compositions over time and alternatively using opioid and SP blockers in well-established analgesic testing methods. Further preclinical and clinical testing is conducted in conformity with governmental drug regulations.

A first aspect of the invention relates to a method of alleviating pain in a patient, comprising administering to a patient in need of such a treatment a therapeutically effective amount of a first compound having opioid receptor agonist activity followed by a therapeutically effective amount of a second compound having opioid receptor agonist activity or a mixture of compounds having opioid receptor agonist activity, or pharmaceutically acceptable salts, esters or prodrugs thereof. The compounds administered may have agonist activity toward the mu, sigma, kappa or delta opioid receptors, including further classified receptor subtypes.

In a preferred embodiment, the compounds having opioid receptor agonist activity are naturally occurring, semi-synthetic or fully synthetic opiate compounds, derivatives or analogs thereof, or pharmaceutically acceptable salts, esters or prodrugs thereof. Naturally occurring opiates are alkaloid compounds that are found in the resin of the opium poppy, and include morphine, codeine and thebaine. Semi-synthetic or fully synthetic opiates include, but are not limited to, dihydromorphine, heterocodeine, dihydrocodeine, dihydrornorphinone, dihydrocodeinone, 3,6-diacetyl morphine, morphinone, 6-desoxymorphine, heroin, oxymorphone, oxycodone, 6-methylene-dihydromorphine, hydrocodone, etorphine, bupemorphine, naloxone or naltrexone.

In other embodiments, the compounds having opioid receptor agonist activity are morphinans or morphinan analogs, which are synthetic opiate analogs, or pharmaceutically acceptable salts, esters or prod rugs thereof. Morphinans or morphinan analogs include, but not limited to, levorphanol, levallorphan, cyclorphan, butorphanol.

In still another embodiment, the compounds having opioid receptor agonist activity are benzomorphan or benzomorphan analogs or derivatives, including pentazocine and cyclazocine, which are synthetic opiate analogs, or pharmaceutically acceptable salts, esters or prodrugs thereof.

In one embodiment, a first compound with opioid receptor agonist activity is administered separately and before the administration of the second compound with opioid receptor agonist activity or a mixture of compounds having opioid receptor agonist activity.

In another embodiment, the first compound having opioid receptor agonist activity is administered in a composition together with the second compound having opioid receptor agonist activity or a mixture of compounds having opioid receptor agonist activity, wherein the first agonist compound is released from the composition into the bloodstream at a faster rate than the second opioid agonist compound or mixture of opioid agonist compounds, so that the first compound binds the corresponding opioid receptor site prior to the second agonist compound or mixture of agonists. In this embodiment, the maximum blood concentration (Cmax) of the first opioid compound will be achieved before the Cmax of the second opioid compound or any component of the mixture of opioid compounds.

In one embodiment, the first opioid receptor agonist and/or the one or more second or subsequent opioid receptor agonists are mu and/or kappa opioid receptor agonists. Compounds that have mu opioid receptor agonist activity or kappa opioid receptor agonist are well known in the art, and methods to determine whether compounds exhibit mu or kappa opioid receptor agonist activity are also known (see, e.g., J. Holaday et al., *Multiple Opioid Receptors: Possible Physiological Functions of mu and delta Binding Sites in vivo*, in Central and Peripheral Endorphis, Basic and Clinical Aspects, 237-250 (A. R. Genazzani & E. E. Miller, eds., 1984); see also Paterson et al., Br. Med. Bull., 39, 31-36 (1983)).

Compounds with mu agonist activity include, but are not limited to, morphine, DAMGO, fentanyl, tramadol, O-demethyl tramadol, methadone, buprenorphine, levorphanol, codeine, and sufentanyl.

Compounds having kappa agonist activity are well known in the art and include, but are not limited to, oxycodone, noroxycodone, oxymorphone, noroxymorphone, butorphanol, cyclazocine, ketazocine, dynorphin, enadoline, nalbuphine, pentazocine, salvinorin A, spiradoline, trifluadom, 4-dichloro-N-Methyl-N-[2-(1-pyrrolidinyl)cyclohexyl]benzeneacetamide (U-50488), U-62066, U-69593, BRL-52537, GR-89696, HZ-2, ICI-204,448, and LPK-26.

In one preferred embodiment of the invention an effective amount of a first kappa opioid receptor agonist is administered to a patient followed by the administration of an effective amount of a mu opioid receptor agonist compound or a mixture of compounds with mu and kappa opioid receptor agonist activity.

In another embodiment, a first compound with mu opioid receptor agonist activity is administered first followed by the administration of a compound with kappa opioid receptor agonist activity or a mixture of compounds with mu and kappa opioid receptor agonist activity.

As discussed above, pre-clinical studies evaluating opioid receptor interactions in rats have indicated that administration of certain selective kappa agonists may block some effects of certain subsequently administered mu agonists (see J. Holaday et al., National Institute on Drug Abuse Research Monograph Series, 71, 173-187 (1986); see also Dosaka-Akita et al., J. Pharmacol. Exp. Ther., 264, 631-637 (1993)). However, it was found that sequential administration of the kappa opioid agonist U•50,488H did not inhibit morphine's effect on increased respiratory rate in a rat model, demonstrating that the cross-reactivity of opioid receptor agonists and antagonists is complex and unpredictable. Furthermore, these publications do not address the effect of sequential administration of opioid receptor agonists and antagonists in human patients.

In one embodiment, the first opioid receptor agonist compound is oxycodone, which is a kappa opioid receptor agonist, and the second or subsequent opioid receptor agonist is the mu receptor agonist morphine, or a mixture of morphine and oxycodone. A particularly preferred embodiment includes the sequential administration of oxycodone followed by administration of a synergistic mixture of morphine and oxycodone.

As discussed above, it has been found that co-administration of sub-antinociceptive doses of oxycodone with morphine to rats results in synergistic levels of antinociception with reduced incidence of side effects (see F. B. Ross & M. T. Smith, Pain, 73, 151-157 (1997); see also F. B. Ross et al., Pain, 84, 421-428 (2000)). Accordingly, in one embodiment a synergistic mixture of morphine and oxycodone comprising morphine to oxycodone in ratio of about 9:1 to about 1:1, morphine to oxycodone by weight is administered after the initial administration of a first opioid receptor agonist. In another embodiment, the synergistic mixture of morphine and oxycodone comprises a mixture of morphine and oxycodone in a ratio of about 5:1 to about 1:1, about 3:1 to about 1:1 or about 2:1 to about 1:1 by weight. In a preferred embodiment, the synergistic mixture comprises a ratio of about 1.5:1 to about 0.5:1, morphine to oxycodone by weight. In a particularly preferred embodiment, the synergistic mixture comprises a ratio of about 1.5:1, morphine to oxycodone by weight.

The absolute amounts of morphine and oxycodone present in the pharmaceutical compositions of the invention or administered in the methods of the invention are not limited and will be determined for a particular patient based on the specific needs of the patient and the type of pain being treated. The specific dose will depend upon a variety of patient-specific factors, including, but not limited to, the age, the body weight, general health, sex, diet, time of administration, rate of excretion, and the judgment of the treating physician and the severity of the condition that requires analgesic treatment. Further, the amount of the active compounds that may be combined with the carrier materials to produce a single dosage form will vary depending upon the patient treated, the purpose of treatment, the pain state and whether the patient is opioid-naive or has developed tolerance. The particular mode of administration will also affect the dose of the compound given to a patient.

Suitable doses of such opioid agonists may be readily determined by those of skill in the art. For example, in the case wherein the mu opioid receptor agonist comprises morphine or an analog or derivative or pharmaceutically acceptable salts thereof, an initial dose of such agonist for a human adult through an intracerebroventricular, epidural or intrathecal route may be between about 0.05 mg and about 0.25 mg per day. It will be appreciated that this dose may be administered in immediate release or controlled-release forms. For example, controlled-release dosage forms may be administered every 12 or 24 hours comprising respectively about 3 or 6 times the four hourly dose given above. In this regard, it is well known that the change from immediate release dosages to controlled release dosages of an opioid is a milligram to milligram conversion which results in the same total "around-the-clock" dose of the opioid (Chemy & Portenoy, *Practical Issues In The Management of Cancer Pain*, in Textbook of Cancer Pain ($3^{rd}$ ed.)).

In some embodiments of the invention, an initial dose of morphine, or analog, or derivative, or pharmaceutically acceptable salts thereof, for a naive human adult through a subcutaneous, intravenous, intramuscular, buccal or sublingual route may be between about 0.5 mg and about 20 mg, about 0.5 mg and about 15 mg, or about 0.5 mg and about 10 mg. In other embodiments, the dose will be between about 0.5 mg and about 5 mg, about 0.5 mg and about 3.5 mg, between about 0.5 mg and about 3.0 mg, between about 0.5 mg and about 2.5 mg, or between about 0.5 mg and about 2.0 mg every four hours.

In other embodiments, an initial dose of morphine, or analog, or derivative, or pharmaceutically acceptable salts thereof, in a controlled release dosage form may be between about 1 mg to about 200 mg, about 1 mg to about 100 mg, about 1 mg to about 50 mg or about 1 mg to about 20 mg. In other embodiments, the initial dose of morphine, or analog, or derivative, or pharmaceutically acceptable salts thereof, in a controlled-release dosage form may be between about 1 mg and about 15 mg, about 1 mg and about 10 mg, between about 1 mg and about 9 mg, between about 1 mg and about 7.5 mg or between about 1 mg and about 6 mg every 12 hours, or between about 3 mg and about 21 mg, between about 3 mg and about 18 mg, between about 3 mg and about 15 mg or between about 3 mg and about 12 mg every 24 hours. In other embodiments comprising controlled-release dosage forms, the initial dose of morphine, or analog, or derivative, or pharmaceutically acceptable salts thereof, may be between about 6 mg and about 75 mg, between about 15 mg and about 60 mg, between about 15 mg and about 45 mg every 12 hours, or between about 12 mg and about 50 mg, between about 30 mg and about 120 mg, or between about 30 mg and about 90 mg every 24 hours.

In other embodiments, an initial dose of morphine, or analog, or derivative, or pharmaceutically acceptable salts thereof, in the pharmaceutical compositions of the invention for a naive human adult through an oral or rectal route is between about 1 mg to about 200 mg, about 1 mg to about 100 mg, or about 1 mg to about 50 mg. In other embodiments, the initial dose of morphine, or analog, or derivative, or pharmaceutically acceptable salts thereof, in a controlled-release dosage form may be between about 2 mg and about 25 mg, between about 5 mg and about 20 mg, or between about 5 and about 15 mg every four hours.

In the case wherein the kappa opioid agonist is oxycodone or analog or derivative or pharmaceutically acceptable salts thereof, a suitable initial dose of such agonist for a human adult through an intracerebroventricular, epidural or intrathecal route may be between about 0.05 mg and about 0.25 mg per day.

In other embodiments, an initial dose of oxycodone, or analog, or derivative, or pharmaceutically acceptable salts thereof, for a naive human adult through a subcutaneous or intravenous route may be between 0.5 mg and about 20 mg, about 0.5 mg and about 15 mg, or about 0.5 mg and about 10 mg. In other embodiments, the initial dose of oxycodone, or analog, or derivative, or pharmaceutically acceptable salts thereof, may be about 1 mg and about 8 mg, between about 1 mg and about 6 mg, or between about 1 and about 4 mg every four hours.

In some embodiments comprising controlled-release dosage forms, an initial dose of oxycodone, or analog, or derivative, or pharmaceutically acceptable salts thereof, may be between about 1 mg to about 200 mg, about 1 mg to about 100 mg, about 1 mg to about 50 mg or about 1 mg to about 20 mg. In other embodiments, the initial dose of oxycodone, or 5 analog, or derivative, or pharmaceutically acceptable salts thereof, may be between about 3 mg and about 24 mg, between about 3 mg and about 18 mg, between about 3 mg and about 12 mg every 12 hours, or between about 6 mg and about 48 mg, between about 6 mg and about 36 mg, or between about 6 mg and about 24 mg every 24 hours.

In additional embodiments, an initial dose of oxycodone, or analog, or derivative, or pharmaceutically acceptable salts thereof, for a naive human adult through an oral or rectal route is between about 1 mg to about 200 mg, about 1 mg to about 100 mg, or about 1 mg to about 50 mg. In other embodiments, the initial dose of oxycodone, or analog, or derivative, or pharmaceutically acceptable salts thereof, may be between about 1 mg to about 25 mg, about 1 mg to about 15 mg, about 1 mg to about 10 mg, about 1 mg and about 8 mg, between about 1 mg and about 6 mg, or between about 1 and about 4 mg every four hours. Alternatively, in some embodiments comprising controlled-release dosage forms, the initial dose of oxycodone, or analog, or derivative, or pharmaceutically acceptable salts thereof, may be between about 3 mg and about 24 mg, between about 3 mg and about 18 mg, between about 3 mg and about 12 mg every 12 hours, or between about 6 mg and about 48 mg, between about 6 mg and about 36 mg, or between about 6 mg and about 24 mg every 24 hours.

Sequential Administration of Opioid Agonist and Non-Opioid Analgesics

In another embodiment, the invention provides a method of alleviating pain in a person in need thereof, comprising administering a therapeutically effective amount of a first compound having opioid receptor agonist activity followed by a therapeutically effective amount of one or more non-opioid analgesic compound(s) or a mixture of one or more nonopioid analgesic compound(s) and one or more compound(s) with opioid receptor agonist activity, or pharmaceutically acceptable salts, esters or prodrugs thereof. Preferably, the first compound with opioid receptor agonist activity will be a mu or kappa opioid receptor agonist including, but not limited to, morphine and oxycodone. In other embodiments, the first compound may be a sigma or delta opioid receptor agonist.

Non-opioid analgesic compounds act to alleviate pain by other mechanisms not associated with binding to an opioid receptor. For example, the non-opioid analgesic compound may be a non-steroidal anti-inflammatory compound (NSAID). NSAID compounds include, but are not limited to, piroxicam, lomoxicam, tenoxicam, salicylic acid (aspirin) and other salicylates such as diflunisal; 2-arylpropionic acids such as ibuprofen, carprofen, fenbufen, fenoprofen, flubiprofen, ketoprofen, ketorolac, loxoprofen, naproxen, oxaprozin, tiaprofenic acid and suprofen; n-arylanthranilic acids such as metenamic acid and meclofenamic acid; arylalkanoic acids such as diclofenac, aceclofenac, acemetacin, etodolac, idomethacin, sulindac and tolmetin and the like, or mixtures thereof.

In another embodiment, the non-opioid analgesic compound is a COX-1 or COX•2 inhibitor compound including, but not limited to, celecoxib (Celebrex®), etoricoxib, lumiracoxib, parecoxib, rofecoxib, valdecoxib, or mixtures thereof.

In still another embodiment, the non-opioid analgesic is a calcium channel binding agent such as gabapentin or pregabalin, or a derivative, analog or prodrug thereof, or mixtures thereof.

In still another embodiment, the non-analgesic compound is gabapentin enacarbil (Solzira™), which is a prodrug of gabapentin with the chemical name 1-[[[[1-(2.Methyl.1-oxopropoxy)ethoxy]carbonyl]amino]methyl]cyclohexaneacetic acid. The structures of gabapentin, pregabalin and gabapentin enacarbil are shown below.

In one embodiment, a first mu or kappa opioid receptor agonist is administered followed by the administration of one or more non-opioid analgesic compounds, or pharmaceutically acceptable salts, esters or prodrugs thereof. In another embodiment, a first mu or kappa opioid receptor agonist is administered followed by the administration of a mixture of one or more compounds with mu or kappa opioid receptor agonist activity and one or more non-opioid analgesic compounds, or pharmaceutically acceptable salts, esters or prodrugs thereof.

In a preferred embodiment, a first kappa opioid receptor agonist is administered to a patient followed by administration of a mixture of one or more mu opioid receptor agonist and one or more non-opioid analgesic compounds, or pharmaceutically acceptable salts, esters or prodrugs thereof. In still another embodiment, a first kappa opioid receptor agonist is administered to a patient followed by administration of a mixture of mu and kappa receptor agonists and one or more non-opioid analgesic compounds, or pharmaceutically acceptable salts, esters or prodrugs thereof.

In a preferred embodiment, the first opioid agonist compound is oxycodone or morphine and the non-opioid analgesic compound is gabapentin, pregabalin or gabapentin enacarbil, or mixtures thereof, or pharmaceutically acceptable salts, esters or prodrugs thereof.

In another embodiment, the invention provides a method and a composition for the alleviation of pain in a patient that comprises the sequential administration of a first agonist compound followed by administration of a second opioid agonist compound, a mixture of opioid agonist compounds, or a mixture of an opioid agonist and a non-opioid analgesic compound, which is followed by the further administration of a third opioid compound, a mixture of opioid compounds, or a mixture of one or more second non-analgesic compounds and one or more opioid compounds.

Sequential Administration of Opioid Agonists and Hybrid Opioid Compounds

In another embodiment, the invention provides a method of alleviating pain in a person in need thereof, comprising administering a therapeutically effective amount of a first compound having opioid receptor agonist activity followed by a therapeutically effective amount of one or more hybrid opioid compound(s) or a mixture of one or more hybrid opioid compound(s) and one or more compound(s) with opioid receptor agonist activity, or pharmaceutically acceptable salts, esters or prodrugs thereof.

In another embodiment, the invention provides a method of alleviating pain in a person in need thereof, comprising administering a therapeutically effective amount of a first compound having opioid receptor agonist activity followed by a therapeutically effective of a mixture of one or more hybrid opioid compound(s) and one or more non-opioid active agents, including non-opioid analgesic compounds, as described above, or pharmaceutically acceptable salts, esters or prodrugs thereof.

Preferably, the first compound with opioid receptor agonist activity will be a mu or kappa opioid receptor agonist including, but not limited to, morphine and oxycodone. In other embodiments, the first compound may be a sigma or delta opioid receptor agonist.

In some embodiments, pharmaceutically acceptable salts, prodrugs or esters of the hybrid opioid compounds may be used.

Hybrid opioid compounds are compounds formed by covalently binding together two or more opioid compounds with a linker component. The linker component may be stable or may hydrolyze under physiological conditions to provide the parent opioid compounds. Hybrid opioid compounds are described in U.S. patent application Ser. No. 13/024,298 ('298 application), filed on Feb. 9, 2011, the disclosure of which is hereby incorporated by reference in its entirety. Hybrid opioid compounds are also described in International Patent Application No. PCT/US2005/000181 ('181 application), filed on Jan. 5, 2005, which is hereby incorporated by reference in its entirety.

In some embodiments, the hybrid opioid compound has greater efficacy in the treatment of pain than an equivalent dose on a molar basis than either of the individual active compounds by itself. For example, a hybrid opioid compound comprising one mole of morphine and one mole of oxycodone will have greater efficacy than two moles of either morphine or oxycodone by themselves.

In another embodiment, the hybrid opioid compound will have fewer undesirable side effects than an equivalent dose on a molar basis of either active compound by itself.

In preferred embodiments, the hybrid opioid compound will have a synergistic efficacy compared to the individual active agents in the treatment of neuropathic pain.

In another embodiment, the hybrid opioid compounds exhibit a synergistic efficacy compared to the individual active agents in the treatment of nociceptive pain.

In still another embodiment, the hybrid opioid compounds exhibit a synergistic efficacy in the treatment of mixed pain states, i.e., a combination of neuropathic pain and nociceptive pain, compared to equivalent doses of the individual active agent alone.

In one embodiment, the hybrid opioid compound will comprise two or more opioid receptor agonists linked by a covalent linker component. In another embodiment, the hybrid opioid compound will comprise an opioid receptor agonist linked to a non-opioid active agent including, but not limited to, a non-opioid analgesic compound as described above. In some embodiments, the non-opioid active agent is gabapentin, pregabalin, or gabapentin enacarbil. In a preferred embodiment, the hybrid opioid compound will comprise two or more opiate compounds bonded together by a covalent linker. The opiate compounds include, but are not limited to, the opiate compounds described above.

As described in the '298 application and in the '181 application, the active compounds may be bonded to the linker components by various chemical bonds, preferably at a position on the active agent that does not impair the biological activity of the active agent. Typically, the active agents are bonded to the linker by a reactive group on the active compound or at a position that may be activated to react with a linker component.

Sequential Administration of Opioid Agonist and Mixed Opioid Salt

In another embodiment, the invention provides a method of alleviating pain in a person in need thereof, comprising administering a therapeutically effective amount of a first compound having opioid receptor agonist activity followed by administering a second or subsequent therapeutically effective amount of a mixed opioid salt that comprises two or more active agents and a polyprotic acid. The active agents may be a mixture of two or more compounds with opioid receptor agonist activity, or a mixture of one or more compound(s) with opioid receptor agonist activity and one or more non-opioid active agents. Mixed opioid salts are described in the '298 application. In general, a mixed opioid salt is a salt of two or more opioid active agents associated together with a pharmaceutically acceptable polyprotic acid or one or more opioid active agent together with one or more non-opioid active agents which are associated with a pharmaceutically acceptable polyprotic acid.

In a preferred embodiment, the mixed opioid salt comprises a first opioid compound and at least a second active agent in combination with a polyprotic acid. In another embodiment, the mixed opioid salt comprises a first opioid compound, a second active agent and a third active agent in combination with a polyprotic acid. In another embodiment, the mixed opioid salt comprises two or more different opioid compounds associated with a polyprotic acid.

In one embodiment, the mixed opioid salt comprises one equivalent of a first compound with opioid receptor agonist activity and one equivalent of a second compound with opioid receptor agonist activity in a mole ratio of 1:1 in combination with a diprotic acid. In another embodiment, the mixed opioid salt comprises one equivalent of a first compound with opioid receptor agonist activity and two equivalents of a second compound with opioid receptor agonist activity in a mole ratio of 1:2, in combination with a triprotic acid. In another embodiment, the mixed opioid salt comprises one equivalent of a first compound with opioid receptor agonist activity, one equivalent of a second compound with opioid receptor agonist activity and one equivalent of a third compound with opioid receptor agonist activity in a mole ratio of 1:1:1, in combination with a triprotic acid.

In a preferred embodiment, the compounds with opioid agonist activity are naturally occurring or synthetic opiate compounds, as described above.

In one embodiment, the mixed opioid salt comprises morphine and at least one other compound with opioid receptor agonist activity. In another embodiment, the mixed opioid salt comprises oxycodone and at least one other compound with opioid receptor agonist activity. In a preferred embodiment, the mixed opioid salt comprises morphine and oxycodone in a 1:1 ratio. In another embodiment, the mixed opioid salt is a sulfate salt of morphine and oxycodone, where the molar ratio of sulfate, morphine and oxycodone is 1:1:1. In another embodiment, the mixed opioid salt comprises morphine and oxycodone with a dicarboxylic acid.

In another aspect of the invention, a mixed salt comprising at least one compound with opioid receptor agonist activity and at least one non-opioid active agent is provided. In one embodiment, the non-opioid active agent is a non-opioid analgesic. Typically, the nonopioid compound will have a basic residue and form a mixed salt with at least one opioid compound and a polyprotic acid, as described above for mixed opioid salts with two opioid compounds. Alternatively, the non-opioid active agent will have an acidic residue that may form a salt in combination with other active agents having basic moieties to form a mixed salt.

In one embodiment, the mixed salt can comprise one or two compounds with opioid receptor agonist activity with one or two non-opioid active agents in various ratios. The compounds with opioid agonist activity may be the same or different and the non-opioid compounds may be the same or different. Similarly to the mixed salts comprising at least two compounds with opioid receptor agonist activity described above, the mixed salt comprising one or two equivalents of an opioid compound and one or two equivalents of a non-opioid compound can exist in mole ratios of 1:1 in combination with a diprotic salt or the opioid compound and non-opioid compound may be in mole ratios of 2:1 or 1:2, in combination with a triprotic acid.

In another embodiment, the non-opioid compound is a calcium channel binding agent such as gabapentin, pregabalin, or gabapentin enacarbil. Both gabapentin and pregabalin have basic amino groups that may form a salt with a polyprotic acid. Gabapentin enacarbil has a free carboxyl group that may be used to prepare a mixed salt with a compound having a basic site.

The sequential administration of the first opioid receptor agonist followed by the administration of the second or subsequent active agents may be achieved by separate administration of a first opioid receptor agonist followed by a later administration of the one or more other active agents. Alternatively, the sequential administration of the first and subsequent compounds may be achieved by using a pharmaceutical composition that comprises an immediate release formulation of a first opioid receptor agonist and a controlled release formulation of one or more active agents, including one or more opioid receptor agonists, one or more non-opioid analgesic compounds, one or more hybrid opioid compounds or one or more mixed opioid salts, or mixtures thereof. Pharmaceutical compositions comprising immediate release or controlled release formulations of opioid drugs are well known in the art. For example, OXYIR® is an immediate release formulation of oxycodone and OXYCONTIN® is a controlled release formulation of oxycodone, which provides controlled delivery of oxycodone over 12 hours.

Accordingly, in one embodiment the invention provides pharmaceutical compositions that comprise an oral dosage form, such as a pill, tablet or capsule, which comprise a controlled release formulation of one or more opioid receptor agonist compounds, a nonopioid analgesic compound, or mixtures thereof, at the core of the dosage form surrounded by an immediate release formulation of a first opioid receptor agonist compound. Thus, the pharmaceutical composition will allow the fast release of a first opioid receptor agonist into the bloodstream and occupation of the corresponding opioid receptor prior to the release of effective amounts of a second or subsequent active agents or mixtures of active agents described above. Any of the opioid receptor agonists and other active agents discussed above may be included in the pharmaceutical compositions, including, but not limited to, the mu and kappa opioid receptor agonists morphine and oxycodone, and the non-analgesic compounds gabapentin, gabapentin enacarbil and pregabalin.

For example, in one preferred embodiment, the pharmaceutical composition will comprise a synergistic mixture of morphine and oxycodone in a controlled release or pulsated release formulation and an immediate release formulation of oxycodone. The immediate release formulation of oxycodone will typically be located at the surface of the composition so that it may be immediately dissolved and released into the bloodstream. In some embodiments, the Tmax, the time required for a compound to reach its maximum concentration in circulation (Cmax), of oxycodone in the immediate release formulation will be from about 10 minutes to about one hour after ingestion. In other embodiments, the Tmax will be from about 10 minutes to about 30 minutes or 45 minutes.

The controlled release formulation of morphine and oxycodone will be released at a slower rate and over a longer period of time. For example, in some embodiments, the controlled release formulation of morphine and oxycodone will release effective amounts of a mixture of morphine and oxycodone over 12 hours. In other embodiments, the controlled release formulation will release effective amounts of morphine and oxycodone over 4 hours or over 8 hours. In still other embodiments, the controlled release formulation will release effective amounts of morphine and oxycodone over 15, 18, 24 or 30 hours.

In some embodiments the later released active agents will be released from the composition in pulses so that pulses of the compounds are released at intervals after ingestion of the composition. For example, in one embodiment, the pulsed release formulation may release a first pulse of the later released active agents about 0.5-1 hour after ingestion, followed by a second pulse after about of 4 hours after ingestion and a third pulse of drug after about 8 hours after ingestion It will be apparent to those skilled in the art that the number of compounds included in the pharmaceutical compositions is not limited to a first compound and second compound or mixture of compounds, and additional compounds may be included.

Pharmaceutical Compositions

The term "pharmaceutically acceptable carrier, adjuvant, or vehicle" refers to a nontoxic carrier, adjuvant, or vehicle that may be administered to a patient, together with a compound of this invention, and which does not destroy or reduce the pharmacological activity thereof.

Pharmaceutically acceptable carriers that may be used in these pharmaceutical compositions are generally known in the art. They include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, solvents, salts or electrolytes, such as protamine sulfate, disodium hydrogen phosphate, potassium hydrogen phosphate, sodium chloride, zinc salts, silicates, colloidal silica, magnesium trisilicate, polyvinyl pyrrolidone, cellulose-based substances, polyethylene glycol, sodium carboxymethylcellulose, polyacrylates, waxes, oils, carbohydrate polymers, polyethylenepolyoxypropylene-block polymers, polyethylene glycol and wool fat. Pharmaceutically accepted vehicles can contain mixtures of more than one excipient in which the components and the ratios can be selected to optimize desired characteristics of the formulation including, but not limited to, shelf-life, stability, drug load, site of delivery, dissolution rate, self-emulsification, control of release rate and site of release, and metabolism.

The compositions of the present invention may be administered orally, parenterally, by inhalation, topically, rectally, nasally, buccally, vaginally, transdermally, or via an implanted reservoir. The term "parenteral" as used herein includes subcutaneous, intravenous, intramuscular, intra-articular, intra-synovial, intrasternal, epidural, intracerebroventricular, intrathecal, intrahepatic, intralesional and intracranial injection or infusion techniques. Preferably, the compositions are administered orally, sub-cutaneously, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents, which are commonly used in the formulation of pharmaceutically acceptable dosage forms including emulsions and suspensions. Other commonly used surfactants, such as Tweens, Spans and other surface-active emulsifying agents or bioavailability enhancers which are commonly used in the manufacture of pharmaceutically acceptable solid, liquid, or other dosage forms, may also be used for the purposes of formulation.

The pharmaceutical compositions of this invention may be prepared by techniques known in the art and may be orally administered in any orally acceptable dosage form including, but not limited to, capsules, tablets, aqueous suspensions or solutions. In the case of tablets for oral use, carriers commonly used include, but are not limited to, celluloses, lactose, or com starch. Lubricating agents, such as magnesium stearate, are also typically added. For oral administration in a capsule form, useful diluents or carriers include lactose and dried cornstarch. When aqueous suspensions or solutions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared using techniques known in the art including, for example, by mixing the agent with a suitable non-irritating excipient, which is solid at room temperature but liquid at rectal temperature, and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, the airways, or the lower intestinal tract. Suitable topical formulations are readily prepared for each of these areas or organs using techniques known in the art. For example, topical application for the lower intestinal tract can be effected in a rectal suppository formulation (see above) or in a suitable enema formulation. Topically-transdermal patches may also be used.

For topical or transdermal applications, the pharmaceutical compositions may be formulated by techniques known in the art in a suitable ointment or base containing the active component suspended or dissolved in one or more carriers. Carriers for topical administration of the compounds of this invention are well known in the art and include, but are not limited to, mineral oil, liquid petrolatum, white petrolatum, propylene glycol, polyoxyethylene, polyoxypropylene compound, emulsifying wax, and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

In addition, the compounds of this invention can be formulated to increase the bioavailability of the compound by methods well known to those of ordinary skill in the art. Methods of formulating the compounds of this invention and examples of formulations are described in *Water-Insoluble Drug Formulation* (R. Liu, ed., 2000), which is incorporated herein by reference in its entirety.

Formulations contemplated as part of this invention include, but are not limited to, nanoparticles formulations made by controlled precipitation methods and by methods disclosed in U.S. patent application Ser. No. 10/392,403 ('403 application), filed on Mar. 20, 2003, which is hereby incorporated by reference in its entirety. Common excipients for nanoparticles known in the art include water, surface active agents such as sugar polymers (modified celluloses) and detergents, and also optionally preservatives such as benzalkonium salts, benzoic acid or salts thereof, or parabens. By forming nanoparticles, the compositions disclosed herein have increased bioavailability. Preferably, the particles of the compounds of the present invention have an effective average particle size of less than about 2 microns, less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 run, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods well known to those of ordinary skill in the art. Nanoparticle preparations can be incorporated into many of the formulation approaches described here, including for example suspensions or creams or ointments for topical or trans dermal administration, suspensions or powders or tablets or capsules or pellets for suppositories or for oral administration, suspensions for sterile injectable formulations, and polymer formulations.

The compounds that make up this invention can be incorporated into biodegradable or non-biodegradable polymers allowing for sustained release of the compound. The polymers can be implanted so that the drug is delivered parenterally throughout the body or the polymers with the compounds that make up this invention can be implanted in the vicinity of a specific area of the body. A review of polymers in controlled drug delivery can be found for example in *Biodegradable Polymers as Drug Delivery Systems* (M. Chasin & R. Langer, eds., 1990), which is incorporated herein by reference in its entirety. Another review can be found in *Handbook of Biodegradable Polymers* (D. Weseman, et al., eds., 1998), which is incorporated herein by reference in its entirety.

In some embodiments, the controlled release formulation is in accordance to controlled release formulations as described in U.S. patent application Ser. No. 13/442,849 ('849 application), filed on Apr. 9, 2012, which is incorporated herein by reference.

A "pharmaceutically acceptable derivative or prodrug" means any pharmaceutically acceptable salt, ester, amide, salt of an ester or amide, or other derivative of a compound of this invention which, upon administration to a recipient, is capable of providing, either directly or indirectly, a compound of this invention or an inhibitor active metabolite or residue thereof. Particularly favored derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, the following derivatives of the present compounds: esters, amino acid esters, amino acid amides, phosphate esters, metal salts, sulfonate esters, carbamates, and amides.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydro iodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate.

Salts derived from appropriate bases include alkali metal (e.g., sodium and potassium), alkaline earth metal (e.g., magnesium), ammonium and $N^+(C_{1-4} \text{alkyl})_4$ salts. This invention also envisions the quaternization of any basic nitrogen-containing groups of the compounds disclosed herein. Water or oil-soluble or dispersible products may be obtained by such quaternization.

Compounds of this invention can also be formulated as mixtures or complexes, including, but not limited to, host-guest complexes with molecules such as cyclodextrins, non-ionic complexes, stabilized amorphous solids, glasses, solid solutions, and co-precipitates. The compound in these formulations can be dispersed to individual molecules, amorphous particles, or crystalline particles. These formulations can be prepared by techniques known to those skilled in the art, including, but not limited to, solvent-mediated co-precipitation, spray-drying, grinding, hot-melt extrusion, and granulation.

The amount of the active compound or compounds, including mixed salts, that may be combined with the carrier materials to produce a single dosage form will vary depending upon the patient treated, the purpose of treatment, the pain state and whether the patient is opioid-naive or has developed tolerance. The particular mode of administration will also affect the dose of the compound given to a patient.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the condition that requires analgesic treatment.

In one embodiment, this invention provides a composition comprising one or more compounds with opioid receptor agonist activity and/or one or more non-opioid analgesic compounds as described above, and a pharmaceutically acceptable carrier, adjuvant or vehicle.

In one embodiment, the carrier is suitable for oral, parenteral, inhalation, topical, or intradermal administration.

In another embodiment, the composition is incorporated into a biodegradable or nonbiodegradable polymer.

In still another embodiment, the composition of comprises one or more compounds with opioid receptor agonist activity and/or one or more non-opioid analgesic compounds as described above and an additive. The additive may be selected from an anti-oxidant, a buffer, a bacteriostat, a liquid carrier, a solute, a suspending agent, a thickening agent, a flavoring agent, a gelatin, glycerin, a binder, a lubricant, an inert diluent, a preservative, a surface active agent, a dispersing agent, a biodegradable polymer, or any combination thereof.

Biological Testing: Assessment of Antinociception

The widely-accepted Tail Flick Latency Test is used to quantify antinociception. This method is described in F. E. D'Armour et al. (J. Pharmacol. Exp. Ther., 72, 74-79 (1941)), which is incorporated by reference in its entirety. Briefly, for oral (po), icv and ip studies, radiant heat is focused on the dorsal surface of the lower third of the rat's tail, whereas for sc studies, noxious heat is applied to the ventral surface of the rat's tail using a Columbus Instruments Analgesia Meter (OH, US). A cut-off of 9.0 s is used to minimize tissue damage. Pre-injection reaction times are typically 3-4.5 s. The mean of three readings taken approximately 5 minutes apart is used. Tail flick latencies are determined at 5, 10, 15, 30, 45, 60, 90, 120 and 180 min. post-dosing, except for sc dosing where the initial tail flick latencies are determined at 10 and 20 min. and testing is ceased at 120 min.

The present invention will be understood more readily by reference to the following examples, which are provided by way of illustration and are not intended to be limiting of the invention.

EXAMPLES

Example 1

Sequential Administration of Oxycodone and Morphine

An initial dose of 10 mg of morphine in a suitable carrier is administered via an intravenous route to a patient requiring intubation. After 30 min., a synergistic combination of doses of 2.0 mg morphine and 2.0 mg of oxycodone are co-injected to the patient. The sequential administration of morphine followed by administration of a mixture of morphine and oxycodone results in a rapid onset of clinical analgesia with no incidence of morphine-induced respiratory depression.

Example 2

Immediate-Release Composition of Oxycodone with Controlled-Release Mixture of Oxycodone-Morphine An oral solid oral dosage form tablet, comprising a core of 5.0 mg oxycodone hydrochloride and 5.0 mg morphine sulfate as active ingredients together with ammonio methacrylate copolymer, hypromellose, lactose, magnesium stereate, polyethylene glycol 400, povidone, sodium hydroxide, sorbic acid, stearyl alcohol, talc, titanium dioxide and triacetin, is prepared according to standard methods known in the art for preparation of tablets. The outside of the tablet is coated with a controlled release formulation comprising 10 mg of oxycodone hydrochloride and gelatin, hypromellose, maize starch, polyethylene glycol, polysorbate 80, red iron oxide, silicon dioxide, dodium laurel sulfate, sucrose, titanium dioxide and yellow iron oxide. The resulting tablet is administered to patients for the alleviation of pain and results in effective analgesia with no incidence of morphine induced respiratory depression.

Example 3

Sequential Administration of Oxycodone and Morphine with a Controlled Release Formulation Controlled release formulations containing 30 mg of morphine sulfate and 20 mg of oxycodone hydrochloride were prepared in the form of tablets. The tablets were comprised of a dry blend of (i) controlled release beadlets, (ii) multiparticulate hydrophilic polymer beadlets that comprise abuse deterrent attributes ("ADF beadlet blend"), and (iii) excipient ingredients, as follows:

TABLE 1

Formulation of tablets (30:20 mg).

| Component | Function | Test Product Quantity (mg) per tablet | % |
|---|---|---|---|
| Controlled release beadlets (30:20 mg) | CR beadlet | 180 | 22.5 |
| ADF beadlet blend | Filler/diluent, abuse deterrent feature | 180 | 22.5 |
| Microcrystalline cellulose, PH102 | Filler/diluent | 317.2 | 39.7 |
| Microcrystalline cellulose, PH200 | Filler/diluent | 79.3 | 9.9 |
| Carbopol 971P | Hydrophilic polymer | 18.1 | 2.3 |
| Croscarmellose sodium | Disintegrant | 22.7 | 2.8 |
| Magnesium stearate | Lubricant | 2.7 | 0.3 |
| Total | | 800.0 | 100 |

The controlled release beadlets comprised a core, a coat, and an enteric coat as follows:

TABLE 2

Formulation of MoxDuo CR beadlets (30:20 mg).

| Component | Function | Test Product Quantity (mg) per unit dose of beadlets | % |
|---|---|---|---|
| Beadlet Core | | | |
| Morphine sulfate | Drug substance | 30.0 | 16.7 |
| Oxycodone hydrochloride | Drug substance | 20.0 | 11.1 |
| Microcrystalline cellulose | Filler/diluent | 44.5 | 24.7 |
| Povidone K30 | Binder | 4.0 | 2.2 |
| Polyoxyl 35 castor oil | Lubricant | 1.5 | 0.8 |
| Purified water* | Process aid | — | — |
| Sub total | | 100.0 | 55.5 |
| Beadlet Coat | | | |
| Ammonio methacrylate copolymer, Type A[1] | Film forming agent | 3.07 | 1.7 |
| Ammonio methacrylate copolymer, Type B[1] | Film forming agent | 27.7 | 15.4 |
| Triethyl citrate | Plasticizer | 3.84 | 2.1 |
| Talc (197) | Antitacking agent | 15.39 | 8.6 |
| Purified water* | Process aid | — | — |
| Sub total | | 50.0 | 27.8 |
| Enteric Coat | | | |
| Methacrylic acid, copolymer dispersion Eudragit L30-D55(2) | Film forming agent | 18.46 | 10.3 |
| Triethyl citrate | Plasticizer | 2.31 | 1.3 |
| Talc (197) | Antitacking agent | 9.23 | 5.1 |
| Purified water* | Process aid | — | — |
| Sub total | | 30 | 16.7 |
| Total | | 180.0 | 100 |

*Removed during drying by evaporation
[1]Expressed as the 30% solids, remaining water removed by evaporation The ADF beadlet blend comprises Carbopol beadlets as the abuse deterrent component (70%), and Meglumine beadlets as a pH modifier (30%). The formulations for the Carbopol beadlets and the Meglumine beadlets are as follows:

TABLE 3

Formulation of Carbopol beadlet.

| Component | Function | Test Product Quantity (mg) per batch | % |
|---|---|---|---|
| Carbopol Beadlet Core | | | |
| Carbopol 971P | Hydrophilic polymer | 300.0 | 8.3 |
| Microcrystalline Cellulose, PH101 | Filler/diluent | 2700.0 | 74.5 |
| Purified water* | Process aid | — | — |
| Sub total | | 3000.0 | 82.8 |
| Carbopol Beadlet Enteric Coat | | | |
| Opadry 20A19301 | Sealer | 150.0 | 4.1 |
| Methacrylic acid, copolymer dispersion, Eudragit L30-D55[1] | Film forming agent | 290.7 | 8.1 |

TABLE 3-continued

Formulation of Carbopol beadlet.

| Component | Function | Test Product Quantity (mg) per batch | % |
|---|---|---|---|
| Triethyl citrate | Plasticizer | 36.4 | 1.0 |
| Talc (197) | Antitacking agent | 145.4 | 4.0 |
| Purified water* | Process aid | — | — |
| Sub total | | 622.5 | 17.2 |
| Total | | 3622.5 | 100 |

*Removed during drying by evaporation
[1]Expressed as the 30% solids, remaining water removed by evaporation

TABLE 4

Formulation of Meglumine beadlet.

| Component | Function | Test Product Quantity (mg) per batch | % |
|---|---|---|---|
| Meglumine Beadlet Core | | | |
| Meglumine | pH modifier | 720.0 | 20.0 |
| Plasdone K-29/32 | Filler/diluent | 90.0 | 2.5 |
| Microcrystalline cellulose, PH101 | Filler/diluents | 2790.0 | 77.5 |
| Purified water* | Process aid | — | — |
| Sub total | | 3600.0 | 82.8 |
| Meglumine Beadlet Enteric Coat | | | |
| Opadry 20A19301 | Sealer | 180 | 4.1 |
| Methacrylic acid, copolymer dispersion, Eudragit L30-D55[1] | Film forming agent | 350.2 | 8.1 |
| Triethyl citrate | Plasticizer | 43.6 | 1.0 |
| Talc (197) | Antitacking agent | 173.2 | 4.0 |
| Purified water* | Process aid | — | — |
| Sub total | | 747.0 | 17.2 |
| Total | | 4347.0 | 100 |

Figure 1:
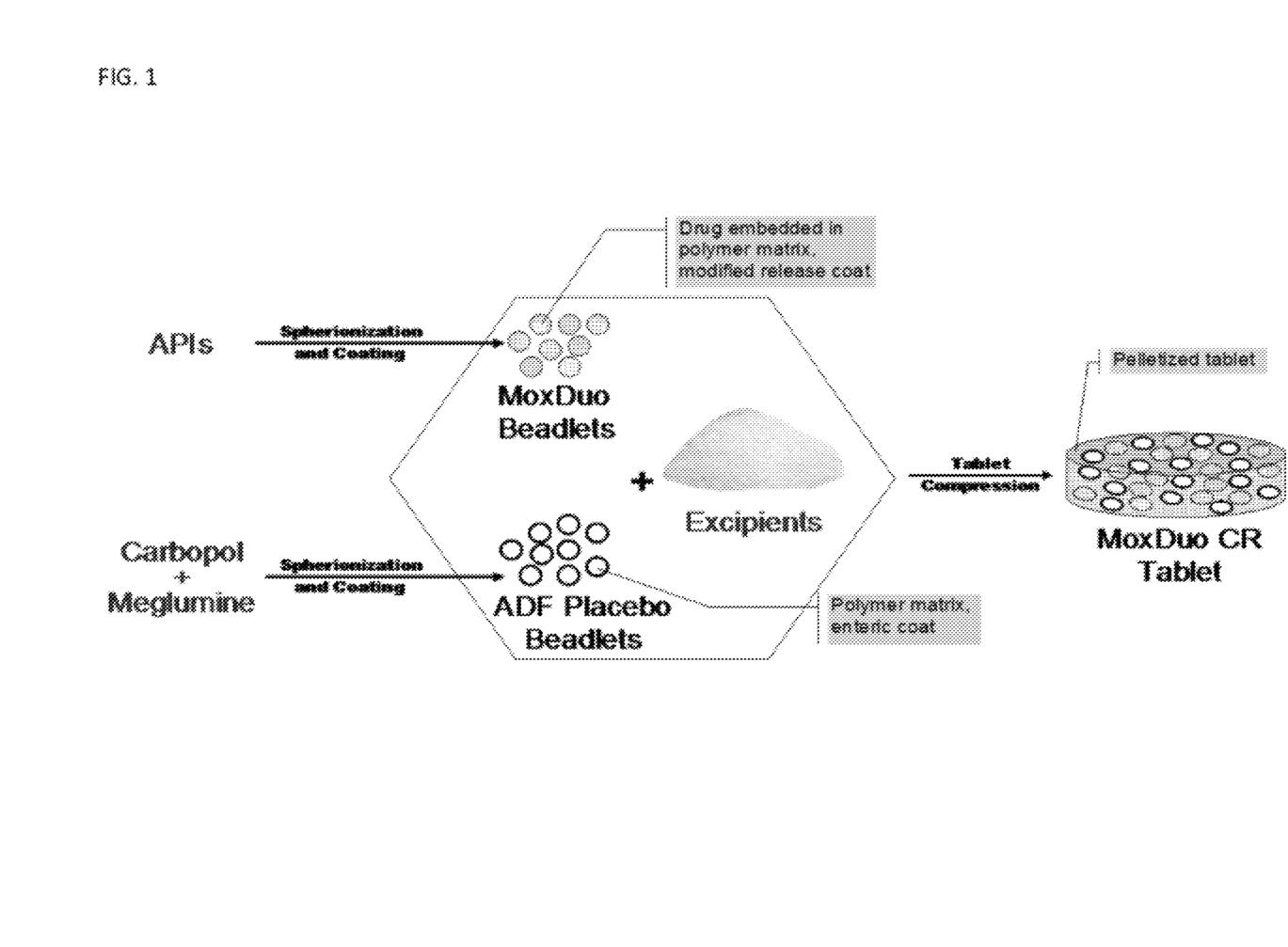
FIG. 1 provides a schematic of the formation of the morphine-oxycodone controlled release tablets.

*Removed during drying by evaporation
[1]Expressed as the 30% solids, remaining water removed by evaporation To prepare the tablets, the dry blend is compressed into tablets using a standard, gravity-feed, pharmaceutical tableting machine, as shown in FIG. 1.

The plasma drug concentration vs. time course profiles and pharmacokinetic parameters of the tablets were assessed in healthy adult humans. Fourteen healthy adult subjects were administered the tablets and blood samples for drug concentration measurements were obtained within 10 minutes prior to each treatment, and at 0.5, 1, 2, 3, 4, 5, 5.5, 6, 6.5, 7, 8, 10, 12, 14, 18, 21, 24, 48, and 72 hours after treatment as a part of a larger study (see the '849 application for a complete description of the study).

Figure 2:
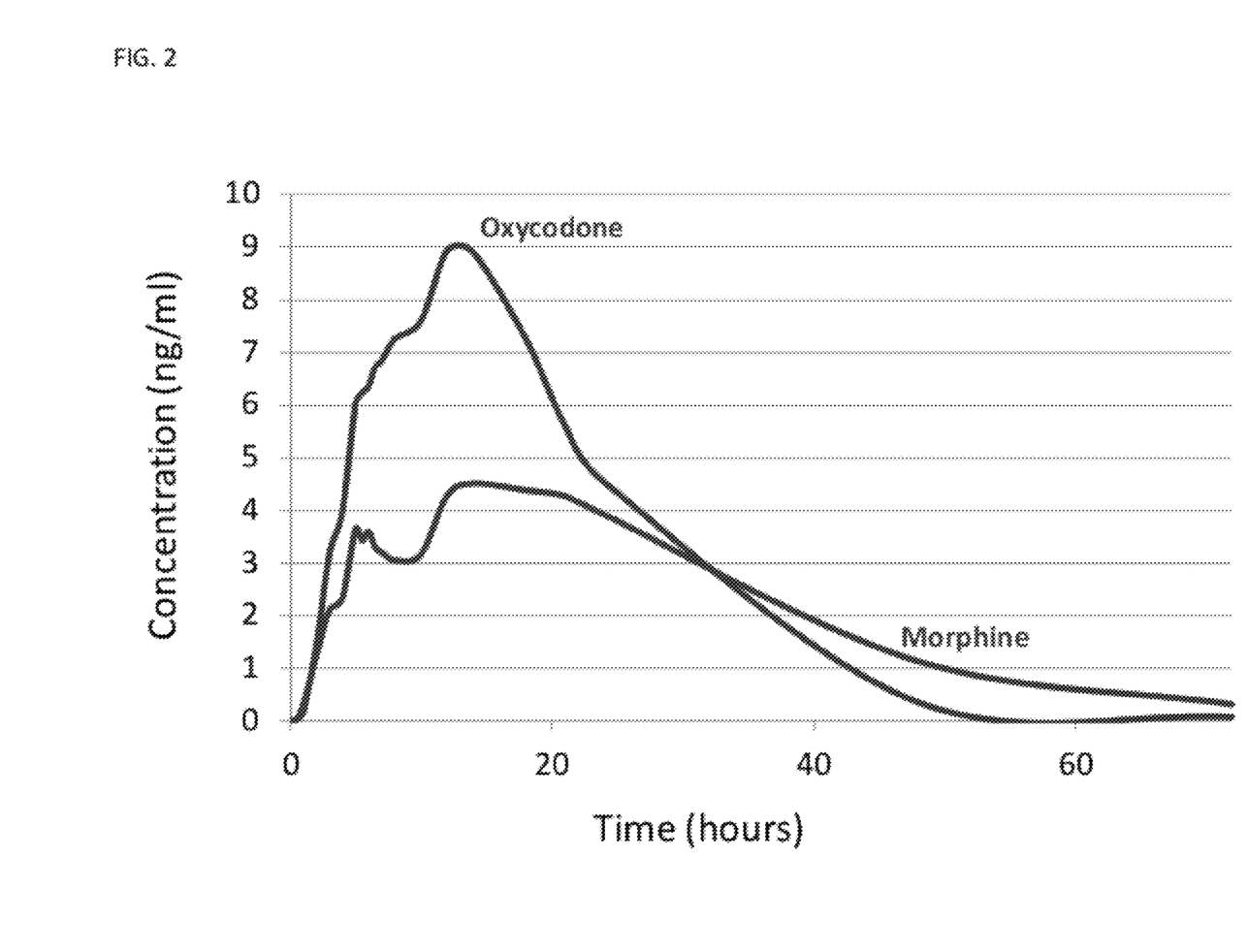
FIG. 2 provides the mean morphine and oxycodone plasma concentrations following single dose administration of the morphine-oxycodone controlled release tablets.

The results indicate that oxycodone is delivered faster and in a greater concentration than the morphine, as shown in FIG. 2 and as demonstrated in Tables 5 and 6. As a result, oxycodone is made available to receptors at a greater rate and to a greater extent than morphine. This demonstrates that the controlled release formulation was capable of delivering oxycodone and morphine sequentially.

TABLE 5

Individual Oxycodone PK Metrics.

| Subject | $AUC_t$ (ng * h/mL) | $C_{max}$ (ng/mL) | $t_{max}$ (h) | $t_{1/2}$ (h) |
|---|---|---|---|---|
| MoxDuo CR tablets (30:20 mg) | | | | |
| 1 | 234.04 | 10.75 | 14.00 | 6.39 |
| 2 | 271.65 | 8.92 | 21.00 | 7.52 |
| 3 | 185.51 | 7.51 | 14.00 | 9.96 |
| 4 | 295.65 | 11.21 | 14.00 | 9.07 |
| 5 | 160.92 | 7.57 | 14.00 | 6.32 |
| 6 | 230.68 | 10.13 | 14.00 | 5.31 |
| 7 | 126.65 | 9.38 | 12.00 | 6.49 |
| 8 | 133.93 | 10.55 | 12.00 | 6.06 |
| 9 | 206.52 | 9.53 | 14.00 | 7.15 |
| 10 | 181.73 | 12.91 | 8.00 | 7.85 |
| Mean | 202.73 | 9.85 | 13.70 | 7.21 |
| SD | 55.95 | 1.65 | 3.20 | 1.43 |

$AUC_t$ = total exposure to the final measurable concentration
$C_{max}$ = peak exposure
$T_{max}$ = time to peak exposure
$t_{1/2}$ = apparent terminal half-life

TABLE 6

Individual Morphine PK Metrics.

| Subject | $AUC_t$ (ng * h/mL) | $C_{max}$ (ng/mL) | $t_{max}$ (h) | $t_{1/2}$ (h) |
|---|---|---|---|---|
| MoxDuo CR tablets (30:20 mg) | | | | |
| 1 | 171.69 | 5.10 | 14.00 | 11.92 |
| 2 | 125.49 | 3.32 | 21.00 | 14.76 |
| 3 | 177.99 | 5.30 | 18.00 | 21.43 |
| 4 | 326.10 | 9.20 | 21.00 | 13.73 |
| 5 | 148.08 | 4.09 | 14.00 | 15.06 |
| 6 | 202.57 | 6.31 | 14.00 | 10.66 |
| 7 | 152.07 | 4.79 | 12.00 | 10.11 |
| 8 | 89.66 | 4.07 | 14.00 | 9.54 |
| 9 | 144.79 | 4.23 | 21.00 | 12.97 |
| 10 | 64.21 | 3.55 | 8.00 | 8.07 |
| Mean | 160.26 | 5.00 | 15.70 | 12.83 |
| SD | 71.19 | 1.72 | 4.40 | 3.80 |

$AUC_t$ = total exposure to the final measurable concentration
$C_{max}$ = peak exposure
$T_{max}$ = time to peak exposure
$t_{1/2}$ = apparent terminal half-life

Having thus described in detail embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for alleviation of pain in a patient in need thereof, comprising sequentially administering to the patient an effective amount of a first compound with opioid receptor agonist activity followed by one or more second or subsequent compounds with opioid receptor agonist activity, wherein the first compound with opioid receptor agonist activity and the one or more second or subsequent compounds with opioid receptor agonist activity are in a ratio of about 1:9 to about 1:1 by weight.

2. The method of claim 1, wherein the one or more second or subsequent compounds with opioid receptor agonist activity comprise a mixed opioid salt.

3. The method of claim 1, wherein the first compound with opioid receptor agonist activity comprises a mu or kappa opioid receptor agonist.

4. The method of claim 3, wherein the first compound with opioid receptor agonist activity comprises a kappa opioid receptor agonist.

5. The method of claim 4, wherein the kappa opioid receptor agonist comprises oxycodone, noroxycodone, oxymorphone, noroxymorphone, butorphanol, cyclazocine, ketazocine, dynorphin, enadoline, nalbuphine, pentazocine, salvinorin A, spiradoline, trifluadom, 4-dichloro-N-Methyl-N-[2-(1-pyrrolidinyl)cyclohexyl]benzeneacetamide (U-50488), U-62066, U-69593, BRL-52537, GR-89696, HZ-2, ICI-204,448, LPK-26, or a combination thereof.

6. The method of claim 1, wherein the one or more second or subsequent compounds with opioid receptor agonist activity comprise one or more mu or kappa opioid receptor agonists.

7. The method of claim 6, wherein the one or more second or subsequent compounds with opioid receptor agonist activity comprise one or more mu opioid receptor agonists.

8. The method of claim 7, wherein the one or more mu opioid receptor agonists comprise morphine, [D-Ala2, N-MePhe4, Gly-ol]-enkephalin (DAMGO), fentanyl, tramadol, O-demethyl tramadol, methadone, buprenorphine, levorphanol, codeine, sufentanyl, or a combination thereof.

9. The method of claim 1, wherein the one or more second or subsequent compounds with opioid receptor agonist activity comprise morphine, fentanyl, sufentanyl, methadone, oxymorphone, or a combination thereof.

10. The method of claim 1, wherein the first compound with opioid receptor agonist activity comprises a kappa opioid receptor agonist, and the one or more second or subsequent compounds with opioid receptor agonist activity comprise mu opioid receptor agonists.

11. The method of claim 10, wherein the kappa opioid receptor agonist comprises oxycodone and the mu opioid receptor agonists comprise morphine.

12. The method of claim 1, wherein the first compound with opioid receptor agonist activity and the one or more second or subsequent compounds with opioid receptor agonist activity are in a ratio of about 1:2 to about 1:1 by weight.

13. The method of claim 12, wherein the first compound with opioid receptor agonist activity and the one or more second or subsequent compounds with opioid receptor agonist activity are in a ratio of about 1:1.5 by weight.

14. A pharmaceutical composition comprising:
(i) an immediate release formulation comprising an effective amount of a first compound having opioid receptor agonist activity; and
(ii) a controlled release formulation comprising an effective amount of one or more compounds having opioid receptor agonist activity, one or more non-opioid analgesic compounds, one or more hybrid opioid compounds, or mixtures thereof, or pharmaceutically acceptable salts, esters or prodrugs thereof;
wherein a therapeutically effective amount of the first compound with opioid receptor agonist activity in the immediate release formulation is released into the blood stream and binds the corresponding opioid receptor before a therapeutic effective amount of the one or more compounds in the controlled release formulation are released into the bloodstream.

15. The pharmaceutical composition of claim 14, wherein the controlled release formulation comprises a mixed opioid salt.

16. The pharmaceutical composition of claim 14, wherein the first compound having opioid receptor agonist activity comprises a mu or kappa opioid receptor agonist.

17. The pharmaceutical composition of claim 16, wherein the first compound having opioid receptor agonist activity comprises a kappa opioid receptor agonist.

18. The pharmaceutical composition of claim 17, wherein the kappa opioid receptor agonist comprises oxycodone, noroxycodone, oxymorphone, noroxymorphone, butorphanol, cyclazocine, ketazocine, dynorphin, enadoline, nalbuphine, pentazocine, salvinorin A, spiradoline, trifluadom, 4-dichloro-N-Methyl-N-[2-(1-pyrrolidinyl)cyclohexyl]benzeneacetamide (U-50488), U-62066, U-69593, BRL-52537, GR-89696, HZ-2, ICI-204,448, LPK-26, or a combination thereof.

19. The pharmaceutical composition of claim 14, wherein the immediate release formulation comprises an effective amount of a first compound having opioid receptor agonist activity, and the controlled release formulation comprises an effective amount of one or more compounds having opioid receptor agonist activity.

20. The pharmaceutical composition of claim 19, wherein the one or more compounds having opioid receptor agonist activity of the controlled release formulation comprise one or more mu or kappa opioid receptor agonists.

21. The pharmaceutical composition of claim 20, wherein the one or more compounds having opioid receptor agonist activity of the controlled release formulation comprise one or more mu opioid receptor agonists.

22. The pharmaceutical composition of claim 21, wherein the one or more mu opioid receptor agonists comprise morphine, [D-Ala2, N-MePhe4, Gly-ol]-enkephalin (DAMGO), fentanyl, tramadol, O-demethyl tramadol, methadone, buprenorphine, levorphanol, codeine, sufentanyl, or a combination thereof.

23. The pharmaceutical composition of claim 19, wherein the one or more compounds having opioid receptor agonist activity of the controlled release formulation comprise morphine, fentanyl, sufentanyl, methadone, oxymorphone, or a combination thereof.

24. The pharmaceutical composition of claim 19, wherein the first compound having opioid receptor agonist activity of the immediate release formulation comprises a kappa opioid receptor agonist, and the one or more compounds having opioid receptor agonist activity of the controlled release formulation comprise mu opioid receptor agonists.

25. The pharmaceutical composition of claim 24, wherein the kappa opioid receptor agonist comprises oxycodone and the mu opioid receptor agonists comprise morphine.

26. The pharmaceutical composition of claim 19, wherein the first compound having opioid receptor agonist activity of the immediate release formulation and the one or more compounds having opioid receptor agonist activity of the controlled release formulation are in a ratio of about 1:9 to about 1:1 by weight.

27. The pharmaceutical composition of claim 26, wherein the first compound having opioid receptor agonist activity of the immediate release formulation and the one or more compounds having opioid receptor agonist activity of the controlled release formulation are in a ratio of about 1:2 to about 1:1 by weight.

28. The pharmaceutical composition of claim 27, wherein the first compound having opioid receptor agonist activity of the immediate release formulation and the one or more compounds having opioid receptor agonist activity of the controlled release formulation are in a ratio of about 1:1.5 by weight.

* * * * *